United States Patent
Ashida et al.

(10) Patent No.: US 8,317,686 B2
(45) Date of Patent: Nov. 27, 2012

(54) ENDOSCOPE

(75) Inventors: Tsuyoshi Ashida, Kanagawa (JP); Takayuki Iida, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 480 days.

(21) Appl. No.: 12/707,532

(22) Filed: Feb. 17, 2010

(65) Prior Publication Data

US 2010/0210908 A1   Aug. 19, 2010

(30) Foreign Application Priority Data

Feb. 18, 2009  (JP) ................. 2009-035585

(51) Int. Cl.
*A61B 17/94*   (2006.01)
(52) U.S. Cl. ...................... 600/148; 600/145
(58) Field of Classification Search ................ 600/144, 600/145, 146, 148, 149, 150, 152
See application file for complete search history.

(56) References Cited

U.S. PATENT DOCUMENTS

| | | | |
|---|---|---|---|
| 7,160,308 B2 * | 1/2007 | Otsuka et al. | 606/130 |
| 7,591,783 B2 * | 9/2009 | Boulais et al. | 600/142 |
| 7,828,725 B2 * | 11/2010 | Maruyama | 600/148 |
| 2002/0032365 A1 | 3/2002 | Hasegawa et al. | |
| 2003/0078475 A1 | 4/2003 | Hirata et al. | |
| 2008/0103362 A1 * | 5/2008 | Couvillon | 600/148 |
| 2009/0227841 A1 * | 9/2009 | Miyako et al. | 600/139 |

FOREIGN PATENT DOCUMENTS

| | | |
|---|---|---|
| EP | 2 098 159 | 9/2009 |
| JP | 11-47082 A | 2/1999 |
| JP | 2000-229061 A | 8/2000 |
| JP | 2001-346756 A | 12/2001 |

* cited by examiner

*Primary Examiner* — Clayton E LaBalle
*Assistant Examiner* — Leon W Rhodes, Jr.
(74) *Attorney, Agent, or Firm* — Birch, Stewart, Kolasch & Birch, LLP (57) ABSTRACT

An endoscope includes a bending section for bending a bending portion, a manipulating section for operating the bending portion to bend the bending portion, a drive section for bending the bending portion with the bending section, a brake instruction section and a brake release instruction section, and a bend amount detecting section. In response to a brake instruction, the bend amount at a point in time the brake instruction was given is detected, and the drive section is so controlled as to maintain the bend amount whereas in response to a brake release instruction, the drive force of the drive section for maintaining the bend amount is gradually reduced.

12 Claims, 5 Drawing Sheets

ENDOSCOPE

BACKGROUND OF THE INVENTION

The present invention relates to an endoscope for use in medical and other fields and more particularly to an endoscope that has achieved a brake for keeping bent a bending portion located at the distal end of an insertion section without resorting to a mechanical configuration using, for example, friction.

As is well known, an endoscope includes an insertion section that is inserted into the human body, a manipulating section for manipulating the insertion section and performing other operations of the endoscope such as air supply/water supply, a connector (LG (light guide) connector) connected to an air supply source, a suction pump, etc., and a universal cord (supply hose) for connecting the connector to the manipulating section and the insertion section.

As disclosed in, for example, JP 11-47082 A, JP 2000-229061 A, and JP 2001-346756 A, an endoscope typically comprises a bending portion close to the distal end of the insertion section such that the bending portion can be bent up and down, and left and right, by turning manipulative knobs provided on the manipulating section.

Generally, bending of the bending portion is achieved by drawing it with a wire.

Specifically, the bending portion comprises numerous rings arrayed and linked in a tubular-form and wires inserted through these linked rings. The rings are linked so that they may pivot (swing) up and down, and left and right, alternately in two orthogonal directions. A total of four wires, two wires spaced apart up down and two wires spaced apart left and right, are inserted through the linked rings; the distal ends of such wires are secured to a ring positioned closest to the distal end.

The manipulative knobs include a UD (up/down) knob for bending the bending portion up and down and an LR (left/right) knob for bending the bending portion left and right.

The two wires inserted through the rings of the bending portion and spaced apart up and down are passed over a pulley that turns integrally with the UD knob. Likewise, the two wires spaced apart left and right are passed over a pulley that turns integrally with the LR knob.

Therefore, by turning either of the manipulative knobs, one of the paired wires linked to the bending portion is withdrawn while the other wire of the pair is advanced to bend the bending portion. The bending portion can be bent to any of the directions including the up and down direction and the left and right direction by manipulating both the UD knob and the LR knob.

The examinations and treatments using an endoscope vary in kind; there are cases where the endoscope needs to be operated with the bending portion kept greatly bent.

Figure 7:
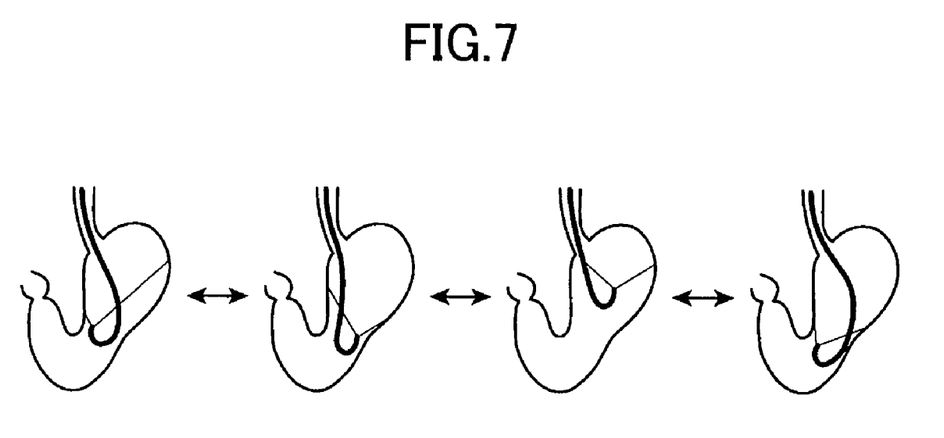
FIG. 7 is a conceptual view for explaining an examination of a gastric fundus with the endoscope.

For instance, as conceptually illustrated in FIG. 7, the gastric fundus is examined by turning the insertion section in the stomach about the axis along which it extends, with the bending portion kept greatly bent.

Thus, in such an examination, a doctor who manipulates the endoscope needs to turn the insertion section while holding a manipulative knob or knobs to keep it from turning backwards by resisting a great counter force while holding the heavy manipulating section. Thus, the doctor must bear an extremely great burden. If the doctor carelessly releases his/her hold on a manipulative knob, the bending portion will return to its straight shape at a stroke due to a strong counter force, which may damage the human body.

As a counter thereto, a typical endoscope is equipped with a so-called brake for keeping the bending portion bent as described also in JP 11-47082 A, JP 2000-229061 A, and JP 2001-346756 A cited above.

A typical brake keeps the manipulative knobs from turning through, e.g., friction, or otherwise mechanically holds in position the manipulating means for the bending portion or the bending means for bending the bending portion, with the bending portion kept bent, thereby to hold the bending portion kept bent by a desired bend amount. Therefore, such a brake may be used to eliminate the load that must be borne to hold the manipulative knobs in position against the counter force produced by the bending portion when performing an operation such as turning the insertion section with the bending portion kept bent.

SUMMARY OF THE INVENTION

Thus, a typical brake provided in an endoscope holds the manipulative knobs or other components in position through friction to hold the manipulating means in position and keep the bending portion bent, thus achieving a brake using a mechanical configuration.

Accordingly, providing a mechanical brake requires the manipulating section to comprise such members as brake knobs for applying a brake and brake members (e.g., brake pads) for holding the manipulative knobs in position through friction, increasing the dimensions and the weight of the manipulating section, a portion held by the operator at all times. Thus, while the conventional brake reduces the load on the operator by aiding in holding the manipulative knobs in position to keep the bending portion bent, it increases load and fatigue on the part of the operator due to the increase in dimensions and weight.

Because such a conventional brake uses friction to keep the bending portion bent, it has another disadvantage that wear, among other things, of the brake members and other components of the brake necessitates adjustments, parts replacement, and the like.

An object of the present invention is to solve the above problems associated with the prior art and provide an endoscope capable of limiting the increase in weight and dimensions of the manipulating section of the endoscope and thus reducing load and fatigue on the part of the operator of the endoscope by achieving a brake that permits keeping the bending portion of the endoscope bent by a desired bend amount not by resorting to a mechanical configuration through friction, etc. but using an electric mechanism using a motor or another drive source and capable, optionally, of reducing load and fatigue on the part of the operator of the endoscope by assisting in the bending operation by using the drive source.

To achieve the above objects, the present invention provides an endoscope having a bending portion close to a distal end of an insertion section and further comprising: bending means for bending the bending portion; manipulating means for performing bending operations of the bending portion; drive means for bending the bending portion with the bending means; bend amount detecting means for detecting a bend amount of the bending portion; brake instructing means for giving a brake instruction to keep the bending portion in a bent state; brake release means for giving a brake release instruction to discontinue maintenance of the bent state; and control means for controlling drive of the drive means, wherein, in response to the brake instruction given by the brake instructing means, the control means acquires the bend amount of the bending portion upon the brake instruction being given from the bend amount detecting means to drive the drive means so as to maintain the bend amount and, when the brake release instruction is given by the brake release means while the bent state is being maintained, gradually reduces a drive force of the drive means.

Preferably, the endoscope further comprises manipulating force detecting means for detecting a manipulating force applied to the manipulating means, wherein the control means assists the bending means in bending the bending portion through the drive means with a force applied with a given ratio to the manipulating force according to the manipulating force detected by the manipulating force detecting means.

It is preferable that when the brake instruction is given by the brake instructing means, the control means gradually reduces an assist drive force of the drive means corresponding to an assist in the bending to "0," and gradually increases a maintenance drive force of the drive means corresponding to the maintenance of the bend amount to maintain the bend amount. Alternatively, upon the brake instruction being given by the brake instructing means, the control means preferably reduces to "0" the assist drive force of the drive means corresponding to the assist in the bending. Alternatively, the control means is preferably provided with a first control mode for gradually reducing to "0" the assist drive force of the drive means corresponding to the assist in the bending in response to the brake instruction by the brake instructing means while gradually increasing the maintenance drive force of the drive means corresponding to the maintenance of the bend amount to maintain the bend amount, and a second control mode for reducing to "0" the assist drive force of the drive means corresponding to the assist in the bending upon the brake instruction being given by the brake instructing means, wherein the endoscope further comprises first selecting means for selecting one of the first control mode and the second control mode, and wherein the control means controls drive of the drive means according to a control mode selected by the first selecting means.

It is preferable that when the brake release instruction is given, the control means gradually increases the assist drive force of the drive means corresponding to the assist in the bending to produce a force with a given ratio to the manipulating force. Alternatively, upon the manipulating force being detected by the manipulating force detecting means after the brake release instruction is given, the control means preferably reduces to "0" the maintenance drive force for the drive means corresponding to the maintenance of the bend amount. Alternatively, the control means is preferably provided with a third control mode for gradually increasing the assist drive force of the drive means corresponding to the bending assist in response to the brake release instruction to produce a force with a given ratio to the manipulating force, and a fourth control mode for reducing to "0" the maintenance drive force of the drive means corresponding to the maintenance of the bend amount upon the manipulating force being detected by the manipulating force detecting means after the brake release instruction is given, wherein the endoscope further comprises second selecting means for selecting one of the third control mode and the fourth control mode, and wherein the control means controls drive of the drive means according to a control mode selected by the second selecting means.

Preferably, the bending means bends the bending portion by withdrawing a wire inserted into the bending portion, and the bend amount detecting means detects the bend amount of the bending portion by detecting an angle of rotation of a pulley over which the wire is passed. Preferably, the bending means bends the bending portion by withdrawing a wire inserted into the bending portion, and the bend amount detecting means detects the bend amount of the bending portion by detecting a displacement of the wire. Preferably, the bend amount detecting means detects the bend amount of the bending portion by detecting an angle of rotation of a gear engaged with the drive means. Preferably, the bend amount detecting means detects the bend amount of the bending portion by detecting a bending angle of the bending portion.

The endoscope of the invention having the above configuration uses an electric mechanism whereby, for example, a pulley used for pulling a manipulating wire is kept at a given rotation angle using a drive source such as a motor to achieve a brake capable of holding the bending portion of the insertion section of the endoscope kept bent by a desired bend amount.

Therefore, as compared with an endoscope having a mechanical brake using friction, the endoscope of the invention permits reduction in the number of used component parts and, hence, reduction in weight and dimensions of the manipulating section and thus reduces load and fatigue on the part of the operator, such as a doctor, operating the endoscope.

Further, according to a preferred embodiment of the invention, the drive source forming a part of the brake may be used to impart a rotative force to the pulley in a given ratio to the manipulating force applied to bending operation means provided for the bending portion or otherwise assist in bending operation and achieves bending with less force, thus favorably reducing load and fatigue on the part of the operator.

DETAILED DESCRIPTION OF THE INVENTION

On the following pages, an endoscope of the present invention is described in detail with reference to the preferred embodiments illustrated in the accompanying drawings.

Figure 1:
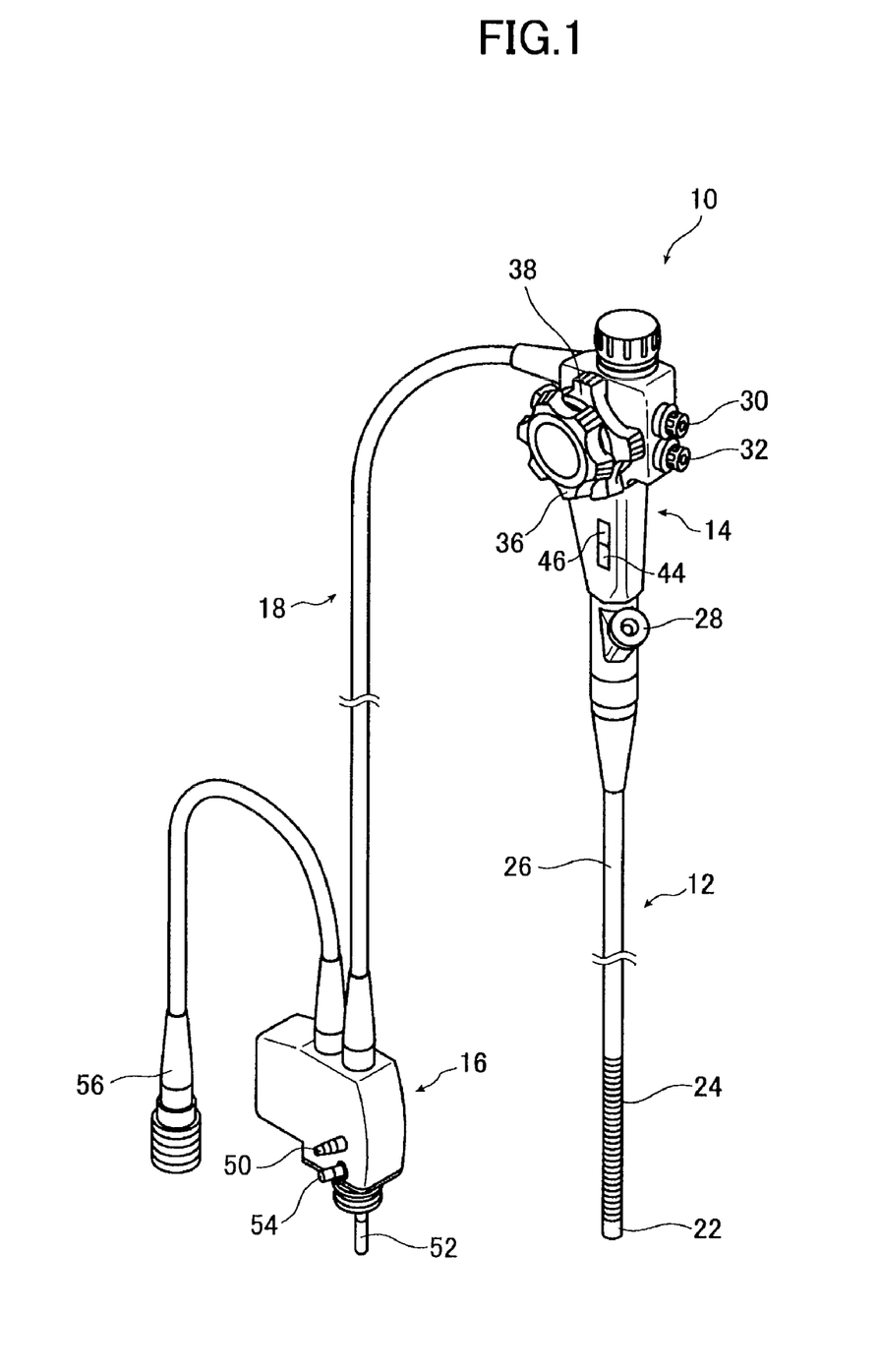
FIG. 1 is a perspective view conceptually illustrating an example of the endoscope according to invention.

FIG. 1 is a schematic view illustrating an example of the endoscope according to the invention.

An endoscope 10 illustrated in FIG. 1 is inserted into an examination region such as a body cavity (e.g. digestive tract) to observe the region, take still or moving images thereof, and even take a tissue thereof, among other objects.

Like a typical endoscope, the endoscope 10 illustrated by way of example includes an insertion section 12, a manipulating section 14, a connector 16, and a universal cord 18.

The endoscope 10 comprises a brake that holds a bending portion 24 kept bent by a desired bend amount (immobilizes the bending operation means) not by resorting to a mechanical configuration using friction to hold the manipulative knobs in position but by using an electric mechanism employing a motor or another drive source. The endoscope 10 further comprises a mechanism for assisting in bending operation using that drive source (a mechanism for providing power-assisted bending operation). Otherwise, the endoscope 10 is basically similar to any known endoscope (endoscopic device).

The insertion section 12 is an elongate part that is inserted into an examination region such as a body cavity, and has a distal end portion 22 at the distal end (the leading end for insertion located opposite from the manipulating section 14), the bending portion 24, and a flexible portion 26.

The distal end portion 22 comprises a lighting glass for providing illumination using a light guide, air/water supply nozzles for withdrawing air from the examination region or for feeding air or water to the region, and a forceps port through which forceps are inserted into the examination region to take a tissue or accomplish other operations.

By way of example, the illustrated endoscope 10 is a so-called electronic scope for taking pictures of the examination region using an image sensor such as a CCD sensor. Thus, the distal end portion 22 comprises an objective lens and a CCD sensor for taking pictures and a circuit board for processing image signals of images taken by the CCD sensor. The endoscope of the invention is not limited to the electronic scope and may be a so-called fiber scope with which the examination region can be directly observed using an optical fiber, etc. In that case, a viewing lens, a viewing window, and the like are provided at the distal end portion 22.

The bending portion 24 is a region that can be bent by operating the manipulating knobs (LR knob 36 and UD knob 38), described later, of the manipulating section 14 in the directions of up, down, left, and right (in four orthogonal directions) in order to insert or locate the distal end portion 22 into or in a desired position.

The flexible portion 26 connects the distal end portion 22 and the bending portion 24 to the manipulating section 14, and is an elongate member that is sufficiently flexible to allow the distal end portion 22 to be inserted into the examination region. The flexible portion 26 and the bending portion 24 accommodate a forceps channel (tube) through which forceps are inserted, air/water supply channels that are connected to the air/water supply nozzles, a light guide for illuminating the examination region, and a cable for transmitting images taken by the CCD sensor (image signals).

The manipulating section 14 is provided to operate the endoscope 10.

As in a typical endoscope, the manipulating section 14 comprises a forceps port 28 through which instruments such as forceps and a clipping tool are inserted, a suction button 30 for performing suction through the air/water supply nozzles provided at the distal end portion 22, and an air/water supply button 32 for supplying air/water through the air/water supply nozzles provided at the distal end portion 22. Since the endoscope 10 is an electronic scope, the manipulating section 14 further comprises a variety of manipulating means, including those for taking pictures of the examination region such as an imaging switch and a zooming switch used when taking still images.

As described above, the manipulating section 14 comprises manipulative knobs for bending the bending portion 24 of the insertion section 12.

Specifically, the manipulating section 14 comprises manipulative knobs for bending the bending portion 24: the LR knob (left/right knob) 36 for bending the bending portion 24 left and right and the UD knob (up/down knob) 38 for bending the bending portion 24 up and down orthogonally to the left and right direction. With the endoscope 10, the LR knob 36 is turned to bend (flex) the bending portion 24 of the insertion section 12 left and right whereas the UD knob 38 is turned to bend the bending portion 24 up and down (direction normal to that in which bending is effected by the LR knob 36), as with various other endoscopes.

The manipulating section 14 further comprises a brake instructing switch 44 (referred to as brake switch 44 below) for applying a brake to hold the bending portion 24 kept bent by a desired bend amount (bending angle) and a brake release switch 46 (referred to as release switch 46 below) for returning the endoscope from a state where the brake is applied to a normal state where the brake is not applied.

The configurations of the manipulative knobs of the manipulating section 14, the configuration of the bending portion 24 and the effects of bending, and the configurations and effects of the brake switch 44, the release switch 46, and the brake (mechanism for holding the bending portion 24 kept bent with a desired bend amount) will be described later in detail.

The connector (LG (light guide) connector) 16 connects the endoscope 10 to water supply means, air supply means, suction means, and the like installed in an endoscope processor; the connector 16 comprises a suction connector 50 for connecting the endoscope 10 to the suction means, a water supply connector for connecting the endoscope 10 to the water supply means, a ventilating connector for connecting the endoscope 10 to the air supply means, and the like.

The connector 16 further comprises an LG rod 52 for connecting the illuminating light guide to a light source provided in the endoscope processor and an S terminal 54 to which an S cord is connected to provide a path for diverting stray current reaching the endoscope 10 when using high frequency treatment tools (so-called electrical scalpels such as a snare and a knife).

The connector 16 is also connected with a video connector 56, which connects the endoscope 10 and a video processor for processing and displaying, for example, images taken by the endoscope 10 (CCD sensor thereof).

The universal cord (LG flexible section) 18 connects the connector 16 to the manipulating section 14.

The light guide, the air/water supply channels, etc., extending from the connector 16 through the universal cord 18, join the manipulating section 14 and, as described above, pass through the flexible portion 26 of the insertion section 12 to join the distal end portion 22.

As described above, the manipulating section 14 comprises the LR (left/right) knob 36 for bending the bending portion of the insertion section 12 left and right and the UD (up/down) knob 38 for bending the bending portion up and down.

Figure 2:
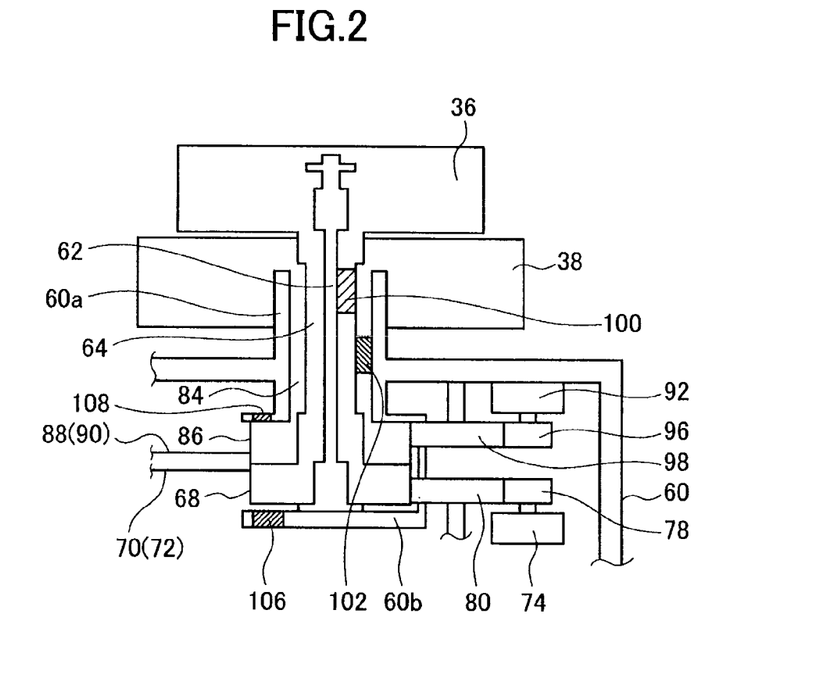
FIG. 2 is a partial schematic view illustrating an example of the manipulating section of the endoscope according to the invention.

FIG. 2 illustrates a schematic view (schematic partial cross section) of an example of configuration of a bending operation mechanism including the LR knob 36 and the UD knob 38 of the manipulating section 14. In the endoscope of the present invention, the bending operation mechanism is not limited to such a configuration, and may use any of known configurations used in various types of endoscopes.

A housing 60 (immovable member) forming the exterior of the manipulating section 14 comprises a cylindrical bearing member 60a that is erected to penetrate the wall plane of the housing 60 and a substantially C-shaped stationary portion 60b provided at the lower end of the bearing member 60a (on the inner lateral end portion of the housing 60).

The stationary portion 60*b* comprises a central columnar shaft 62 that is erected to pass through the center of the bearing member 60*a* and project outward from the housing 60.

A linking tube (rotary shaft) 64 is secured to the underside of the LR knob 36, and a pulley 68 is secured to the lower end of the linking tube 64 so as to be contained in the stationary portion 60*b*. Two wires 70 and 72 are passed over the pulley 68 to bend the bending portion 24 left and right (alternatively, the ends of the wires 70 and 72 are secured to the pulley 68).

Further, bend amount detecting means 106 is provided in the stationary portion 60*b* to detect the bend amount of the bending portion 24 in the left and right direction from the rotation angle of the pulley 68. The bend amount detecting means 106 will be described later in detail.

The wires 70 and 72 are provided to bend the bending portion 24 left and right (angle wires/manipulating wires) and, as will be described (see FIG. 4), are inserted into the bending portion 24 in such a manner that they are spaced apart left and right by a wire guide or the like; the ends of the wires closer to the distal end portion 22 are secured to a distal end ring 112 of the bending portion 24. With the endoscope 10, rotation of the LR knob 36 causes the pulley 68 to turn, and one of the wires 70 and 72 is withdrawn and the other wire is advanced depending on the direction of rotation of the pulley 68 to bend the bending portion 24 left and right.

The linking tube 64, which is cylindrical, has the central shaft 62 passed therethrough and is rotatably supported on the central shaft 62.

Therefore, both the LR knob 36 and the pulley 68 are also rotatably supported on the central shaft 62 about its central axis. When the LR knob 36 is turned by the operator, the pulley 68 turns by the same amount as the LR knob 36 so that one of the wires 70 and 72 is withdrawn and the other wire is advanced.

The pulley 68 has also a gear (not shown) for engaging with an LR brake motor 74 (referred to as LR motor 74 below).

The LR motor 74 is drive means forming a part of the brake for applying a brake to the bending portion 24 in the left or right direction (a brake for holding the bending portion 24 kept bent in the left or right direction); the LR motor 74 is secured to the housing 60 of the manipulating section 14 with a stay, etc. not shown. A gear 78 is secured to the rotary shaft of the LR motor 74. A gear 80 is pivotally supported in the housing 60. The gear 80 meshes with the gear 78 of the rotary shaft of the LR motor 74 and a gear formed on the pulley 68.

Therefore, the pulley 68 is turned by a torque delivered upon actuation of the LR motor 74. Thus, one of the wires 70 and 72 is withdrawn and the other is advanced depending upon the direction of rotation of the pulley 68 as will be described to bend the bending portion 24 left and right while driving the LR motor 74 with a constant output to apply a brake to the leftward or rightward bending of the bending portion 24 (in other words, a torque is applied to the pulley 68 to enable the bending portion 24 to be kept bent left or right). Should the LR knob 36 be manipulated with a brake applied, the brake can be kept applied (a set bent state that is assumed when the brake is applied) through, for example, positioning control such that the LR motor 74 is driven so as to cancel out the manipulating force.

In the illustrated example of the endoscope 10, the LR motor 74 may be used to assist in manipulating the LR knob 36 directly connected through the linking tube 64 to the pulley 68, i.e., in manipulation to bend the bending portion 24 left and right.

The brake applied to the bending and the assist in the bending will be described later in detail.

In the manipulating section 14 of the endoscope 10, the UD knob 38 is located beneath the LR knob 36 (between the LR knob 36 and the housing 60).

The UD knob 38 comprises a recess on the underside thereof. The linking tube (rotary shaft) 84 is secured to the ceiling surface of the recess. A pulley 86 is secured to the lower end of the linking tube 84 so as to be contained in the stationary portion 60*b*. Two wires 88 and 90 connected to the bending portion 24 to withdraw and bend the bending portion 24 are passed over the pulley 86.

The bend amount detecting means 108 is provided in the stationary portion 60*b* to detect the upward or downward bend amount of the bending portion 24 from the rotation amount of the pulley 86. The bend amount detecting means 108 will be described later in detail.

The wires 88 and 90 are provided to bend the bending portion 24 up and down and are inserted into the bending portion 24 in such a manner that they are spaced apart up and down (direction normal to that in which the wires 70 and 72 are spaced apart from each other) by a wire guide; the ends of the wires closer to the distal end portion 22 are secured to the distal end ring 112 of the bending portion 24. In the endoscope 10, rotation of the UD knob 38 causes the pulley 86 to turn, so that one of the wires 88 and 90 is withdrawn and the other wire is advanced depending on the direction of rotation of the pulley 86 to bend the bending portion 24 up and down.

The linking tube 84 is a cylindrical member through which the linking tube 64 secured to the LR knob 36 passes and is inserted through the bearing member 60*a* of the housing 60 so as to be pivotally supported by the linking tube 64. With the linking tube 64 passing through the linking tube 84, the pulley 86 located at the lower end of the linking tube 84 is disposed on the top of the pulley 68 located at the lower end of the linking tube 64 of the LR knob 36.

Hence, both the LR knob 38 and the pulley 86 are pivotally supported by the linking tube 64 about the linking tube 64. When the LR knob 38 is turned by the operator, the pulley 86 also turns by the same amount as the LR knob 36 so that one of the wires 88 and 90 is withdrawn and the other wire is advanced.

As described above, the linking tube 64 or the LR knob 36 turns about the central shaft 62. Consequently, the linking tube 84, i.e., the UD knob 38, also turns about the central shaft 62 and, therefore, the LR knob 36 and the UD knob 38, provided to bend the bending portion 24, turn about the same axis.

Like the pulley 68 described above, the pulley 86, which is provided for upward and downward bending, has also a gear (not shown) for engaging with a UD brake motor 92 (referred to as UD motor 92 below).

The UD motor 92 is drive means forming a part of the brake for applying a brake to the bending portion 24 in the up and down direction (a brake for holding the bending portion 24 kept bent upwards or downwards); the UD motor 92 is secured to the housing 60 of the manipulating section 14. A gear 96 is secured to the rotary shaft of the UD motor 92. A gear 98 is pivotally supported on the housing 60. The gear 98 meshes with the gear 96 of the rotary shaft of the UD motor 92 and a gear formed on the pulley 86.

Thus, a torque is delivered upon actuation of the UD motor 92, causing the pulley 86 to turn, so that one of the wires 88 and 90 is withdrawn while the other is advanced depending upon the direction of rotation of the pulley 86 to bend the bending portion 24 up and down. Further, by continuously driving the UD motor 92 with a constant output, a brake can be applied to the upward and downward bending of the bending portion 24 (in other words, a torque is applied to the pulley 86 to enable the bending portion 24 to be kept bent up or down). Should the UD knob 38 be manipulated with a brake applied, the brake can be kept applied (a set bent state that is assumed when the brake is applied) through, for example, position control such that the UD motor 92 is driven so as to cancel out the manipulating force.

Further, by driving the UD motor 92, assist can be provided in manipulating the UD knob 38 directly connected through the linking tube 84 to the pulley 86, i.e., in manipulation to bend the bending portion 24 up and down.

The brake applied to bending and the assist in bending will be described later in detail.

In the case illustrated in FIG. 2, the number of revolutions produced by the LR motor 74 and the UD motor 92 is reduced by providing the gears 80 and 98 between the LR motor 74 and the UD motor 92 forming a part of the brake for the bending portion 24, but the present invention is not limited thereto; a planetary gear or a harmonic drive may be provided in an auxiliary motor (motor head) to reduce the number of revolutions produced by the LR motor 74 and the UD motor 92 or a gear may be additionally used as means for reducing the speed.

In the example illustrated in FIG. 2, a brake is applied to the bending portion 24 by transmitting the rotation of the LR motor 74 and the UD motor 92 through the gears 78, 80, 95, and 98 to turn the pulleys 68 and 86 (linking tubes=manipulative knobs) but the invention is not limited thereto; a brake may be applied to the bending portion 24 using a direct drive motor (DD motor).

Figure 3:
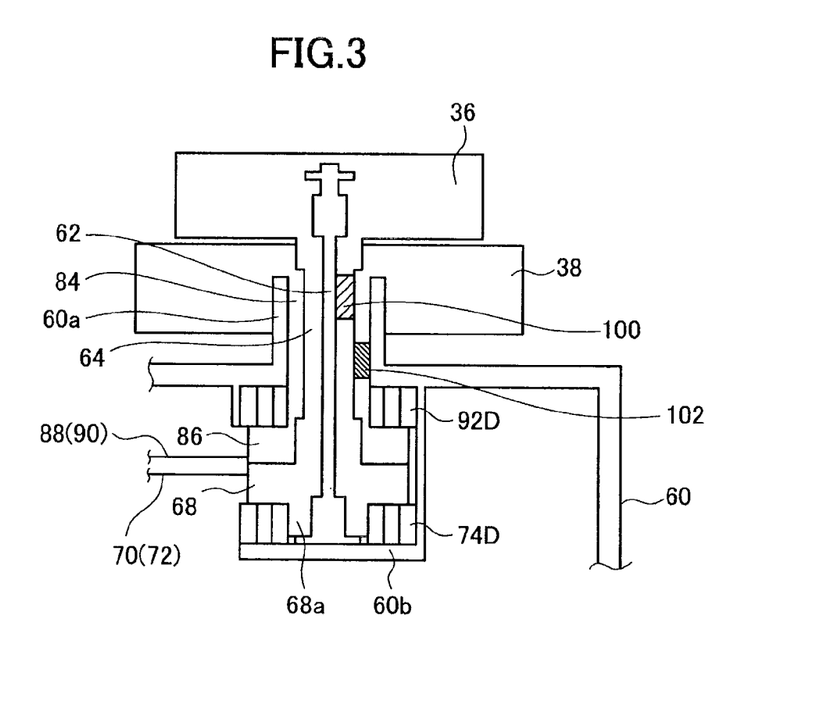
FIG. 3 is a partial schematic view illustrating another example of the manipulating section of the endoscope according to the invention.

For example, the configuration illustrated in FIG. 2 is drawn upon to provide a configuration as illustrated in FIG. 3 comprising a cylindrical portion 68a formed at the lower part of the pulley 68 for bending the bending portion 24 left and right. An inner rotor type DD motor is used as an LR motor 74D, whose rotor is engaged with the cylindrical portion 68a. The LR motor 74D turns the cylindrical portion 68a, thereby bending the bending portion 24 left and right while applying a torque to the pulley 68 to hold the bending portion kept bent.

An inner rotor type DD motor is used as a UD motor 92D also for upward and downward bending. The linking tube 84 is passed through the rotor of the UD motor 92D and engaged therewith. The UD motor 92D turns the linking tube 84, thereby bending the bending portion 24 up and down while applying a torque to the pulley 86 to hold the bending portion kept bent.

In the manipulating section 14, the stationary portion 60b of the housing 60 comprises, as described earlier, the bend amount detecting means 106 for detecting the rotation angle of the pulley 68 corresponding to the leftward or rightward bending of the bending portion 24 and the bend amount detecting means 108 for detecting the rotation angle of the pulley 86 corresponding to the upward or downward bending of the bending portion 24.

With the endoscope 10, the bending of the bending portion 24 is achieved in such a manner that the manipulative knobs are turned to rotate the pulleys 68 and 86 and pull one of the two wires spaced apart from each other in the bending direction while advancing the other depending on the direction of rotation of the pulleys. Accordingly, the angle of rotation (rotation amount) of the pulleys 68 and 86 corresponds to the bend amount of the bending portion 24, and thus detection of the angle of rotation of the pulleys 68 and 86 results in detecting the bend amount of the bending portion 24.

The manipulating section 14 has a torque sensor 100 positioned in the hatched area of the linking tube 64 for sensing the torque applied to the linking tube 64. As described above, the LR knob 36, the linking tube 64, and the pulley 68 turn integrally. Thus, the torque sensor 100 is detecting means for detecting the manipulating force (rotary torque) applied to the LR knob 36.

A torque sensor 102 is provided in the hatched position of the linking tube 84 to detect the torque applied to the UD knob 38. Likewise, the UD knob 38, the linking tube 84, and the pulley 86 turn integrally. Thus, the torque sensor 102 is detecting means for detecting the manipulating force applied to the UD knob 38.

According to a preferred embodiment, the torque sensors 100 and 102 are provided to assist in bending the bending portion 24. In the illustrated example of the manipulating section 14, the torque sensors 100 and 102 each form a part of the cylindrical linking tubes that are directly connected to the respective manipulative knobs for bending and which turn integrally with the respective manipulative knobs (or are each provided in a part of the respective linking tubes) to directly detect the manipulating forces applied to the manipulative knobs to bend the bending portion 24.

With the illustrated example of the endoscope 10, the bending amount of the bending portion 24 at a given point in time is detected from the angle of rotation of the pulleys 68 and 86 detected by the bend amount detecting means in response to a brake instruction given by the brake switch 44, and the drive of the LR motor 74 and the UD motor 92 is controlled so as to maintain the bend amount at that point in time thereby to apply a brake to the bending of the bending portion 24. This will be described later in detail.

With the illustrated example of the endoscope 10 according to a preferred embodiment, the manipulating forces applied to the manipulative knobs are detected by the toque sensors 100 and 102, and the LR motor 74 and the UD motor 92 are driven to turn the pulleys 68 and 86 with given forces in given ratios to the respective manipulating forces to assist in bending the bending portion 24.

According to the present invention, there is no specific limitation to the bend amount detecting means 106 and the bend amount detecting means 108, and any known means may be used to detect the angle of rotation (or amount of rotation).

By way of example, cuts like those of a gear may be formed at given intervals on the periphery of the pulleys 68 and 86, whereas an optical sensor comprising a light emitting unit and a light receiving unit separated from each other in the direction normal to that in which the pulleys 68 and 86 turn may be disposed in a position corresponding to the cuts to provide an optical encoder for detecting the angle of rotation from the number of times the cuts have passed the optical sensor. When such an optical sensor is used with the illustrated example of the endoscope 10, the teeth formed on the pulleys 68 and 86 may be used as cuts for detecting the angle of rotation.

Besides the optical encoder, a potentiometer (variable resistor) may be suitably used to detect the angle of rotation.

According to the present invention, the bend amount of the bending portion 24 need not necessarily be detected from the angle of rotation of the pulleys 68 and 86.

By way of example, the displacement of the wires 70 and 72 corresponding to the leftward and rightward bending and the displacement of the wires 88 and 90 corresponding to the upward and downward bending also correspond to the bend amount of the bending portion 24 like the angle of rotation of the pulleys 68 and 86. Therefore, the bend amount of the bending portion 24 may be detected by detecting the displacement of the wires. The displacement of the wires may be detected by any of known detection methods as appropriate including an optical method, a mechanical method, and a method using magnetism.

In lieu of the pulleys 68 and 86, the bend amount of the bending portion 24 may be detected by detecting the angle of rotation of the gears 78 and 80 and gears 96 and 98 directly or indirectly meshing with the pulleys 68 and 86. The angle of rotation of the gears 78 and 80 and the gears 96 and 98 may be detected by similar methods to those used for the pulleys 68 and 86.

Figure 5:
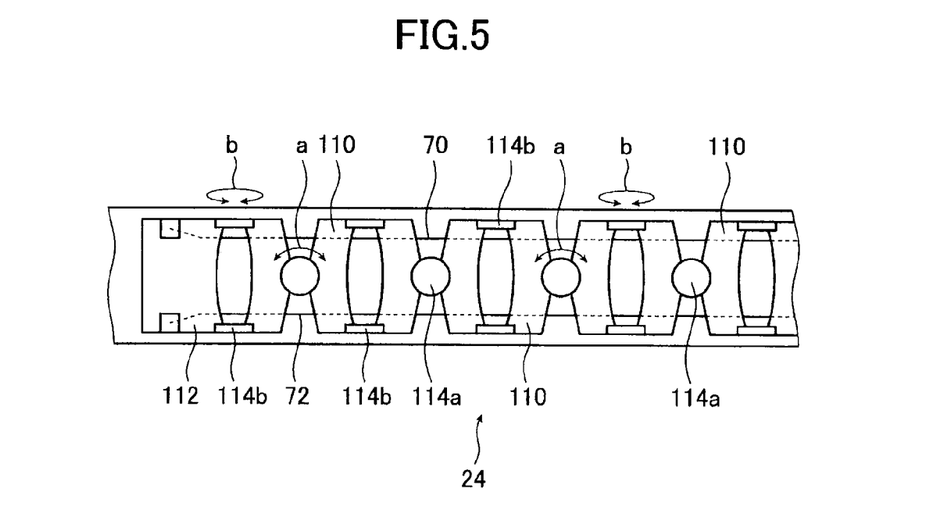
FIG. 5 is a schematic view illustrating an example of the bending portion that may be used in the endoscope according to the invention.

Further, the bend amount of the bending portion 24 may be detected by detecting the angle of the bending portion 24. There is no specific limitation to the method of detecting the angle of the bending portion 24; for example, the bend amount of the bending portion 24 may be determined by measuring the amount of strain produced in an elastic cover forming an outer sheath of the bending portion 24 at a position between two adjacent circular rings 110. The amount of deformation of the elastic cover may be detected using known means such as a strain gage of a type using electric resistance wire.

Further, a plurality of methods for detecting the bend amount may be used in combination or a plurality of methods for detecting the bend amount may be provided to permit selection of a method therefrom.

The torque sensors 100 and 102 provided in the linking tube 64 and the linking tube 84 are not limited in any manner and may be any of various known torque sensors including a torque sensor that uses a strain gage and a magnetostrictive torque sensor.

According to the present invention, the manipulating force for bending need not necessarily be detected by detecting the torque of the linking tube 64 and the linking tube 84; for example, one may detect the torque of the pulley 68, the gear 80 or various other portions or positions to directly or indirectly detect the manipulating force for bending the bending portion 24. Further, various sensing means other than the torque sensors 100 and 102 may be used to detect the manipulating force.

Figure 4:
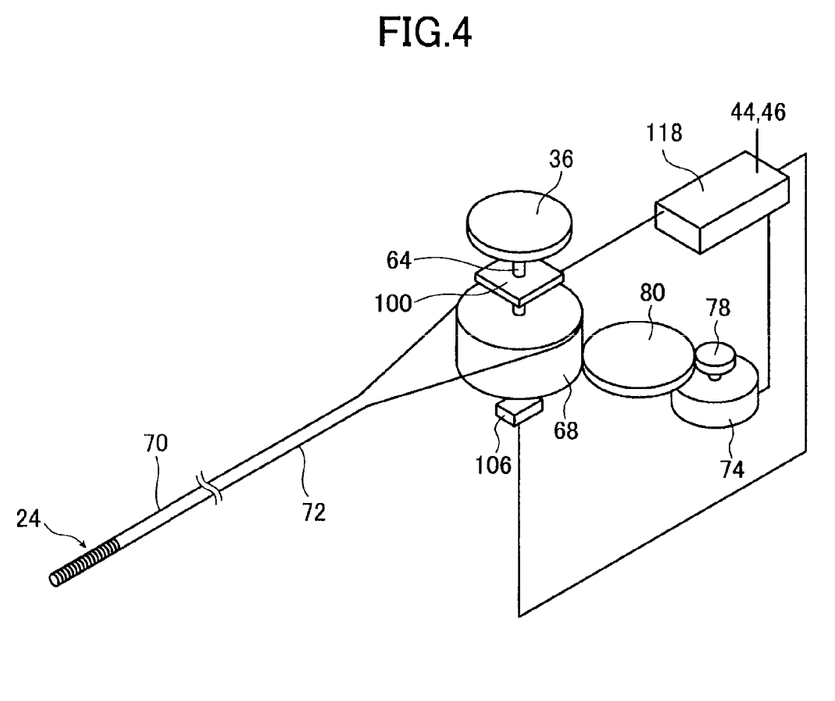
FIG. 4 is a view conceptually illustrating a bending mechanism of the bending portion of the endoscope of FIG. 1.

FIG. 4 is a conceptual view of a bending mechanism for bending the bending portion 24 left and right according to the example illustrated in FIG. 2; FIG. 5 is a conceptual view of an example of the bending portion 24. In FIG. 4, a reference numeral 118 indicates control means, not shown in FIG. 2, for controlling the drive of the LR motor 74 (and the UD motor 92).

Note that the bending mechanism for bending the bending portion 24 of the endoscope according to the invention is not limited to the illustrated case; one may use various other means (bending mechanisms) for bending the bending portion 24 generally employed in endoscopes. The configuration of the bending portion 24 is also not limited to the illustrated example, and all designs generally adopted in endoscopes can be used.

The illustrated example of the bending portion 24 comprises, by way of example, a total of nine rings: eight circular rings 110 and one distal end ring 112.

As illustrated in FIG. 5, each circular ring 110 is a substantially tubular member having, when viewed from one lateral direction, an outwardly curved plane on one side thereof and an inwardly curved plane on the other side in its axial direction. The outwardly and inwardly curved planes each have space on both sides thereof in the axial direction. The distal end ring 112 is a substantially cylindrical member and is located closest to the distal end portion 22 of the bending portion 24.

The circular rings 110 and the distal end ring 112 are linked to each other by linking members 114*a* and linking members 114*b*.

The circular rings 110 are arranged in such a manner that the directions in which the rings are curved outwards and inwards alternate in the longitudinal direction of the insertion section 12. Each linking member 114*a* links adjacent circular rings 110 at the center of both outwardly curved sides so that the circular rings can pivot (swing) left and right (in the directions indicated by the arrow "a"). Each linking member 114*b* links adjacent circular rings 110 and the leading circular ring 110 and the distal end ring 112 at both ends of the inwardly curved sides so that the circular rings can pivot (swing) up and down (in the directions indicated by the arrow "b").

The linking members 114*a* and linking members 114*b* are disposed alternately to link the circular rings 110. Thus, the circular rings 110 are linked so as to be pivotable up and down and, alternately, left and right.

The wires 70 and 72 for bending the bending portion 24 left and right are guided and spaced apart left and right (in the up and down direction in the drawing) by a wire guide, not shown, as they penetrate the circular rings 110. By way of example, the distal end of the wire 70 is secured to the inner right-hand side of the distal end ring 112, and the distal end of the wire 72 is secured to the inner left-hand side of the distal end ring 112.

Though not illustrated in FIG. 5, the two wires 88 and 90 for bending the bending portion 24 up and down are guided and spaced apart up and down (normal to the drawing) by the wire guide as they penetrate the circular rings 110. By way of example, the distal end of the wire 88 is secured to the inner upper side of the distal end ring 112, and the distal end of the wire 90 is secured to the inner lower side of the distal end ring 112.

As described above, the LR knob 36, one of the manipulative knobs for bending, is turned to rotate the linking tube 64 and the pulley 68. One of the wires 70 or 72 is withdrawn while the other is advanced depending on the direction of rotation of the pulley 68, and the bending portion 24 is bent left or right, with the withdrawn wire on the inner side. The greater the amount by which the wire 70 or 72 is withdrawn, that is, the greater the amount of rotation of the pulley 68, the greater the degree by which the bending portion 24 is bent.

Therefore, the bend amount (bending angle) of the bending portion 24 can be adjusted by controlling the amount by which the LR knob 36 is turned.

The endoscope 10 of the invention comprises an electrical brake (brake mechanism) for the bending portion 24 using a drive source such as a motor and an assist mechanism for assisting in bending the bending portion 24 and comprises the brake switch 44 for instructing application of brake to the bending portion 24, the release switch 46 for releasing an applied brake, the torque sensor 100 (102), the bend amount detecting means 106 (108), the LR motor 74 (UD motor 92), and the control means 118 for controlling the drive of the motor.

Referring to FIG. 4, a detailed description will be made of the effects of the torque sensor 100, the bend amount detecting means 106, the control means 118, and the brake applied to the bending portion 24 in the endoscope 10.

While the description to follow is provided referring to FIG. 4 to explain the brake for holding the leftward or rightward movement of the bending portion 24 (a mechanism that holds the bending portion 24 kept bent left or right), the brake and the assist in bending are likewise performed for upward and downward bending. The same applies to the assist in bending the bending portion 24 described later.

The result of measurement of the angle of rotation of the pulley 68 given by the bend amount detecting means 106 is supplied at all times to the control means 118.

In response to the signal generated upon the brake switch 44 being depressed, the control means 118 detects and stores the angle of rotation of the pulley 68 at a point in time the brake switch 44 is depressed (i.e., the bend amount of the bending portion 24 at that point in time) and controls the LR motor 74 to maintain the stored angle of rotation.

There is no limitation to the method of controlling the drive of the LR motor 74 for maintaining the stored angle of rotation; one may use any of various methods, such as the PID control, using the angle of rotation as target value.

When bent, the bending portion 24 tends to return to its linear state, i.e., a state where it is not bent, or a straight state, due to its counter force and automatically returns to the straight state by such counter force when the hand is released from the LR knob 36. Therefore, by storing the angle of rotation of the pulley 68 at the point in time the brake switch is applied and driving the LR motor 74 to turn the pulley 68 with a value of electricity that maintains that angle of rotation, the counter force of the bending portion 24 and the torque of the LR motor 74 counterbalance each other to hold the bending portion 24 thus bent and keep the brake applied without the need to apply any manipulating force to the LR knob 36.

Should the LR knob 36 be manipulated to change the bend amount of the bending portion 24 with a brake applied, the bending portion 24 can be kept bent, that is, the brake can be kept applied as the position control or the like is effected to drive the LR motor 74 so as to cancel out the manipulating force of the LR knob 36 or reverse the manipulation.

As described above, the manipulating section 14 also comprises the release switch 46 for releasing the brake and returning the bending portion 24 to its normal straight state.

In response to a signal generated upon the release switch 46 being depressed, the control means 118 stops driving the LR motor 74, releases the linking tube 64 from a torque applied thereto, and releases the bending portion 24 from a brake applied thereto so it returns to its normal straight state.

In response to a signal from the release switch 46, the control means 118 does not immediately stop the drive of the LR motor 74 but slowly reduces the drive current (drive force (output)) of the LR motor 74 to gradually reduce the bending angle of the bending portion 24, thus ensuring that the bending portion 24 gently returns to its straight state.

Should the drive of the LR motor 74 keeping the bending portion 24 bent be stopped immediately, the bending portion 24, kept bent, immediately returns to its straight state by the counter force, possibly causing injuries to a human body or other accidents. In contrast, the bending portion 24 can be gently returned to its straight state by gradually reducing the drive current of the LR motor 74, thereby preventing injuries to a human body or other accidents that could be caused if the bending portion 24 returns to its straight state immediately.

Although the above examples use the value of the drive current provided by the LR motor 74 (UD motor 92) to control the drive force of the LR motor 74 (UD motor 92), the invention is not limited this way. For example, the drive voltage of the motor may be used as means for controlling the drive force of the LR motor 74. When the LR motor 74 is turning at a low rotary speed, the drive voltage and the drive current are generally directly proportional to each other. With the endoscope 10 of the invention, the rotary speed of the LR motor 74 for bending the bending portion 24 is basically so low that the drive voltage and the drive current are directly proportional to each other. With the endoscope 10 of the invention, therefore, not only the drive current but also the drive voltage may be suitably used to control the drive of the LR motor 74.

Although the LR motor 74 is used as driving means for applying a brake to the bending portion 24 in the endoscope 10 of the illustrated example, the present invention is not limited this way. For example, various other driving means may be used including a solenoid that uses a fluid pressure or an electromagnetic force to assist in pulling action.

Since, according to the invention, a drive force such as the LR motor 74 is thus used to maintain the bend amount at a point in time a brake is applied by position control, etc., no brake knob and no brake member (e.g., brake pad) are required to apply a brake and, as compared with an endoscope having a mechanical brake using friction, the endoscope of the invention permits reduction in the number of component parts, which reduces the weight and dimensions of the manipulating section and hence reduces the load and fatigue on the part of the operator such as a doctor manipulating the endoscope.

As described above, the illustrated example of the endoscope 10 permits application and release of brake in the up and down direction as well as in the left and right direction and, when the bending portion 24 is bent by both the LR knob 36 and the UD knob 38, the application/release of brake, when instructed, is effected in both directions.

Alternatively, the application/release of brake in the left and right direction may be effected independently of the application/release of brake in the up and down direction.

Further, the illustrated example of the endoscope 10 permits application of brake in both the up and down, and the left and right directions in a preferred embodiment, but the present invention is not limited this way.

That is, according to the endoscope of the present invention, the electric brake mechanism may be used only in the left and right direction or in the up and down direction while using a conventional mechanical brake mechanism using friction in the other directions.

As described above, the endoscope 10 comprises the LR motor 74 corresponding to leftward and rightward bending and the UD motor 92 corresponding to upward and downward bending for applying a brake to the bending portion 24.

A preferred embodiment of the endoscope 10 illustrated by way of example uses these components and further comprises the torque sensor 100 for detecting the torque applied to the linking tube 64, i.e., the manipulating force applied to the LR knob 36 and the torque sensor 102 for detecting the torque applied to the linking tube 84, i.e., the manipulating force applied to the UD knob 38 thereby to assist in bending the bending portion 24.

Now, the bending assist effected by the LR motor 74 will be likewise described with reference to FIG. 4 taking an example of manipulation of the LR knob 36 for bending the bending portion 24 left and right.

In the endoscope 10, the control means 118 detects, at given intervals (sampling timing), the result of measurement of a torque given by the torque sensor 100, i.e., the manipulating force (manipulating torque $T_H$) applied to the LR knob 36.

Based upon the detected manipulating torque $T_H$, the control means 118 works out a torque (motor torque $T_M$) to be applied by the LR motor 74, i.e., an assist amount given by the LR motor 74. By way of example, let k be a proportional constant for obtaining the assist amount, then;

$$T_M = kT_H.$$

Upon calculating the motor torque $T_M$, the control means 118 calculates a current I needed to obtain the motor torque $T_M$. Specifically, let $K_T$ be the specific torque constant of the motor, the current I is obtained as $$I=(1/K_T)T_M$$

from the property "$T_M=K_T I$" of the motor. Alternatively, the current I may be obtained from a table previously prepared that gives a relationship between the torque of the LR motor 74 and the current.

The control means 118 drives the LR motor 74 by constant current control to drive the LR motor 74 with the current I.

Thus, the load on the operator manipulating the bending of the bending portion 24 of the endoscope 10 can be lessened according to the proportional constant k that determines the assist amount.

By way of example, let $T_L$ be the torque (manipulating force) required to bend the bending portion 24 by an intended bend amount when no assist is provided by the LR motor 74.

When the above assist is provided, $$T_L=T_H+T_M.$$

Now, because $T_M=kT_H$, $$T_L=kT_H+T_H=(1+k)T_H$$

Therefore, $$T_H=[1/(1+k)]T_L$$

Thus, the torque the operator needs to apply for bending the bending portion 24 is lessened to 1/(1+k). Accordingly, when the LR motor 74 always provides an assist with the same force as the manipulating torque applied by the operator (k=1), the torque the operator needs to apply can be reduced to 50% of the torque required for bending.

Thus, when basic bending operations are performed by a doctor and, specifically, when an assist is provided by the LR motor 74 in withdrawing the wires 70 and 72, that is, in bending the bending portion 24, according to the torque (manipulating force applied to the manipulating means) applied by a doctor to the LR knob 36 to turn the LR knob 36, the insertion section 12 can be safely retracted using the LR knob 36 to manipulate the bending of the bending portion 24 even in case of, for example, a blackout or a failure of the LR motor 74.

Further, since the bending of the bending portion 24 is basically performed with the aid of the manipulating means such as the LR knob 36, the operator can perform bending operations while feeling the counter force the bending portion 24 receives from a location under examination, which optimally prevents accidents such as perforation and makes delicate operations easy to perform.

When providing such bending assist, the control means 118 may be adapted to ensure that the drive forces of the LR motor 74 and the UD motor 92 for providing an assist upon depression of the brake switch 44 are 0 and use the position control or the like to apply a brake to the bending of the bending portion 24. In other words, upon depression of the brake switch 44, the LR motor 74 and the UD motor 92 may be driven with only a drive force corresponding to the brake.

When a bending assist is provided, the torque for bending the bending portion 24 is the sum of the torques produced by the LR motor 74 and the UD motor 92, both being the drive sources, and the torque of the manipulating force produced by the operator. When application of brake is instructed by the brake switch 44, therefore, a brake, if accomplished immediately, may quickly change the output of the LR motor 74 and the UD motor 92, causing the operator to have an unnatural feeling from the change. To prevent this from occurring, the control means 118 may be adapted to gradually reduce to 0 the drive currents of the LR motor 74 and the UD motor 92 corresponding to the assist while gradually increasing the drive currents of the LR motor 74 and the UD motor 92 corresponding to the brake to achieve application of brake to the bending of the bending portion 24.

Alternatively, there may be provided a mode in which the drive currents of the LR motor 74 and the UD motor 92 for providing an assist are reduced to 0 upon depression of the brake switch 44 and another mode in which the drive currents of the LR motor 74 and the UD motor 92 corresponding to an assist are gradually reduced to 0 upon depression of the brake switch 44 while gradually increasing the drive currents of the LR motor 74 and the UD motor 92 corresponding to a brake, so that the operator may choose between these modes using switching means, selecting means, and the like.

With the endoscope 10 of the invention, when the brake is released upon depression of the release switch 46, the drive currents (drive force) of the LR motor 74 and the UD motor 92, both being the drive sources, are gradually reduced to release the brake as described above.

With the endoscope 10 having a bending assist function, when a bending operation is performed with a manipulative knob (that is, when the torque sensor detects a torque produced by the bending operation) at a moment in time while the drive currents of the LR motor 74 and the UD motor 92 are being gradually reduced in response to the release of a brake (during a period from the start of reduction of the drive currents until the time the output becomes 0, i.e., while a brake is being released), the drive currents of the LR motor 74 and the UD motor 92 corresponding to the brake may be reduced to 0 immediately at that point in time while driving the LR motor 74 and the UD motor 92 with drive currents corresponding to only the bending assist. In other words, at a point in time the bending operation is effected while the brake is being released, the LR motor 74 and the UD motor 92 may be driven from that point in time with only a drive force corresponding to the assist.

When providing a bending assist, the operator may have an unnatural feeling as in the case described earlier, should the drive currents corresponding to the brake be immediately reduced to 0 at a point in time the bending operation is effected while the brake is being released. To prevent this from occurring, therefore, the gradual reduction of the drive currents of the LR motor 74 and the UD motor 92 for applying a brake may be continued according to the instruction for releasing the brake while gradually increasing the drive currents of the LR motor 74 and the UD motor 92 corresponding to the assist in bending.

Alternatively, there may be provided a mode in which the drive current corresponding to a brake is reduced to 0 at a point in time a bending operation is performed while the brake is being released and another mode in which the drive current for releasing the brake is gradually reduced and the drive current for providing an assist is gradually increased, so that the operator may choose between these modes using switching means, selecting means, and the like.

The operation of applying a brake to the bending portion 24 and, optionally, the bending assist may be achieved using a computer and software or a control system that may have any of a variety of configurations.

Figure 6A:
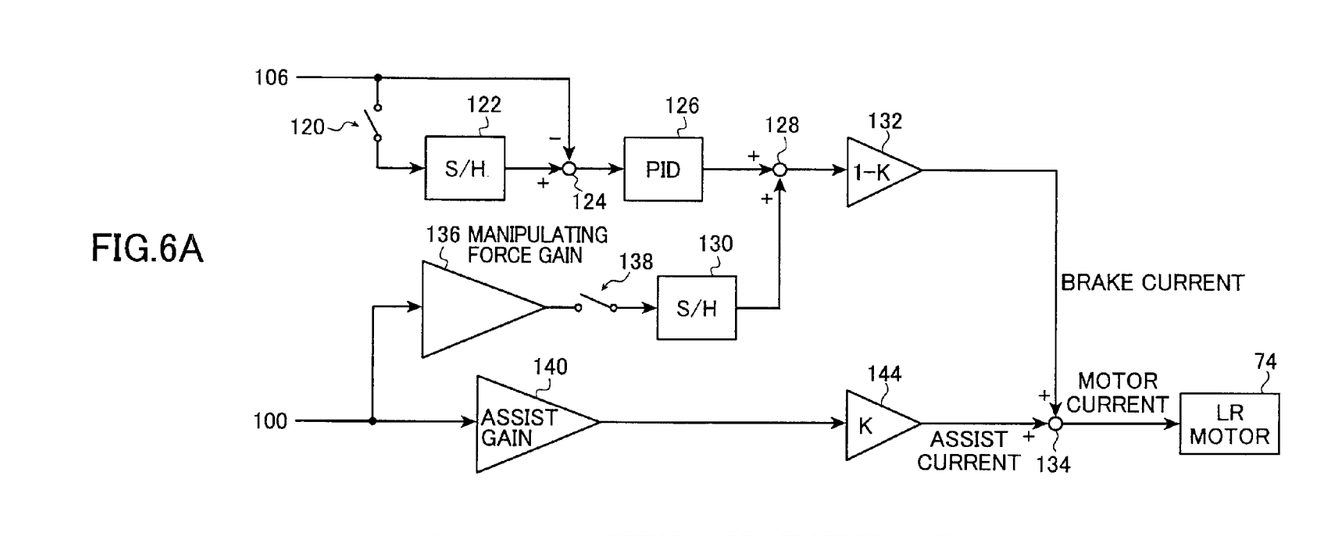
FIG. 6A is a block diagram illustrating an example of control system of the endoscope of FIG. 1.

FIG. 6A is a conceptual block diagram of an example of control system that effects a control such that, upon depression of the brake switch 44 (brake ON) in the endoscope 10, the drive electricity (drive force) for the LR motor 74 for bending assist is gradually reduced while the drive electricity for the LR motor 74 for braking is gradually increased, whereas, upon depression of the release switch 46 (brake OFF), the drive electricity (drive force) for the LR motor 74 for bending assist is gradually increased to provide an assist with a given ratio to the manipulating force. FIG. 6A illustrates an example only for leftward and rightward bending but upward and downward bending can also be likewise achieved as in the examples described earlier.

The control system illustrated in FIG. 6 comprises a first switch 120, a first sample hold (S/H) circuit 122, a first adder 124, a PID controller 126, a second adder 128, a second sample hold circuit 130, a first amplifier 132, a third adder 134, a manipulating force gain amplifier 136, a second switch 138, an assist gain amplifier 140, and a second amplifier 144.

In FIG. 6A, the upper half of the diagram represents a part of the control system related to braking; the lower half (ending with the second amplifier 144) is related to the assist in bending the bending portion 24.

When no brake is applied (brake OFF), the first switch 120 and the second switch 138 are on (connected).

Therefore, the output signal (electric current) of the bend amount detecting means 106 is sent to the sample hold circuit 122 and the first adder 124.

The output signal (electric current) of the torque sensor 100 is sent to the assist gain amplifier 140 and the manipulating force gain amplifier 136.

When the brake is off, K in the first amplifier 132 and the second amplifier 144 is "1."

Figure 6B:
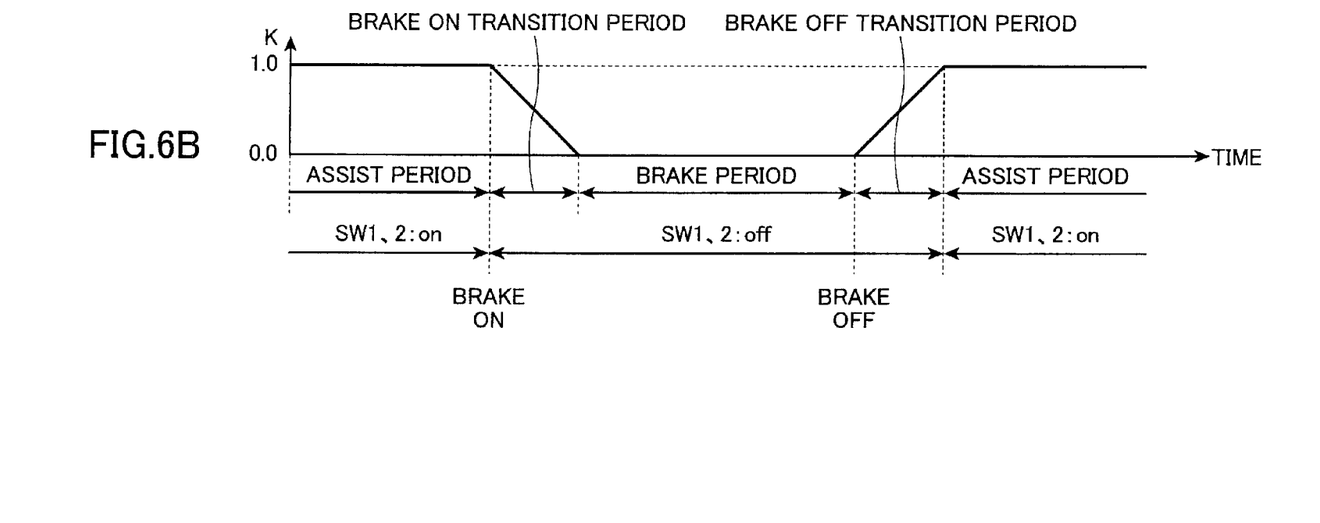
FIG. 6B is a graph for explaining coefficients of the amplifiers in the block diagram.

Since the coefficient in the first amplifier 132 is "1−1=0," the electricity (brake current) from the brake system for position control of the bend amount is 0, and only the current for bending assist (assist current) is supplied to the LR motor 74 as drive current or motor current (assist period in FIG. 6B).

Specifically, the assist gain amplifier 140 multiplies the output signal of the torque sensor 100 by a coefficient that varies according to the proportional constant k which determines the bending assist amount to obtain a current value corresponding to the torque for bending assist, which current value is multiplied by 1 in the second amplifier 144 to produce an assist current, whereupon the third adder 134 adds the assist current and the brake current 0 to produce a motor current, which is supplied to the LR motor 74.

In this state, the manipulating force gain amplifier 136 multiplies the output signal it receives from the torque sensor 100 by a coefficient "k+1" that varies with the proportional constant k set in the assist gain amplifier 140 to produce a current value required to maintain the bending observed at that moment, which current value is sent to the second sample hold circuit 130.

As it appears from the above equations, while an assist is being provided, the manipulating torque $T_H$ produced by the operator and the torque $T_M (=kT_H)$ generated by the LR motor 74 balance with the torque $T_L$ required to bend the bending portion 24. Thus, in this state, "$T_L=(1+k)T_H$" holds. Accordingly, the output of the manipulating force gain amplifier 136 can be made equal to the torque required to keep the bending of the bending portion 24 by setting a gain (coefficient) for multiplying the manipulating torque $T_H$ by "1+k" in the manipulating force gain amplifier 136.

When the brake switch 44 is depressed (brake ON) in this state, the first switch 120 and the second switch 138 are turned off (disconnected), and the current value supplied at this point in time is stored in the first sample hold circuit 122 and the second sample hold circuit 130. Specifically, the first sample hold circuit 122 stores as target current value the output signal of the bend amount detecting means 106 at a point in time the brake is turned on; the second sample hold circuit 130 stores a current value required to keep the bend amount at the point in time the brake is turned on.

The first sample hold circuit 122 continues to output the target current value to the first adder 124. As described earlier, the first adder 124 is also supplied with the output signal of the bend amount detecting means 106. The first adder 124 calculates and sends the difference between the two values to the PID controller 126, which uses the difference to calculate a drive current value (position control current value) for driving the LR motor 74 required to maintain the target value and sends the drive current value to the second adder 128.

Therefore, while the operator manipulates the LR knob 36 to maintain the bending, the position control current value is 0.

The second sample hold circuit 130 continues to output the stored current value to the second adder 128.

The second adder 128 adds the position control current value sent from the PID controller 126 and the current value sent from the second sample hold circuit 130 required to maintain the bending and produces the output to the first amplifier 132. The first amplifier 132 multiplies the current value by the coefficient "1−K" to produce a brake current, which is outputted to the second adder 134.

The second adder 134 adds the assist current and the brake current to produce a motor current, which is supplied to the LR motor 74.

The first amplifier 132 and the second amplifier 144 each comprises time constant control means, not shown, to start gradually reducing K from "1" to "0" upon the brake being turned on as illustrated in FIG. 6B.

Even when the brake is turned on, the second amplifier 144 continues to produce an assist current while such gradual reduction of K causes the brake current for applying a brake (maintaining the bending) to increase gradually to reach a current value for maintaining the bend amount at a point in time the brake is turned on whereas the assist current for the bending assist gradually decreases to become 0 (brake ON transition period in FIG. 6B).

Thus, the above configuration permits a smooth transition from the assist current to the brake current, i.e., from a part of the current required to maintain the bending to the whole current required to maintain the bending, and a smooth transition of the drive force (assist force) for the LR motor 74 corresponding to the manipulating force produced by the operator to 0. This can prevent the operator from having an unnatural feeling caused by, for example, a quick change in output of the LR motor 74.

When K in the first amplifier 132 and the second amplifier 144 becomes 0, the coefficient in the second amplifier 144 becomes 0, causing the assist current to become 0. Therefore, the motor current sent from the second adder 134 to the LR motor 74 is the sum of the current value outputted from the second sample hold circuit 133 for maintaining the bend amount at a point in time the brake is turned on and the position control current value for maintaining the bend amount outputted from the PID controller 126 at the target value. In brief, the motor current sent from the second adder 134 to the LR motor 74 is only the brake current (brake period).

When the brake is kept on (brake on), depression of the release switch 46 (brake OFF) first causes K in the first amplifier 132 and the second amplifier 144 to gradually increase from "0" to "1" as illustrated in FIG. 6B.

As described above, the brake current is the sum of a position control current value and a current value required to maintain the bending. Therefore, starting to gradually increase K at the same time as turning the brake off causes the brake current for braking to gradually decrease to "0" contrary to when the brake is on, so that the assist current for bending assist gradually increases to become a current value corresponding to the bending assist (brake OFF transition period=brake release period).

Thus, the above configuration permits a smooth transition from the brake current to the assist current, i.e., from the whole current required to maintain the bending to a part of the current required to maintain the bending and a smooth transition of the drive force applied to the LR motor 74 for braking to 0, even when the operator performs bending operation while the brake is being released. This prevents the operator from having an unusual feeling as in the case described earlier.

Further, when the operator does not perform bending operation while the brake is being released, the bending portion 24 in the state of bending can be returned from its state assumed when the brake is on to its straight state gently and smoothly.

When K in the first amplifier 132 and the second amplifier 144 becomes "1," that is, when the brake current becomes "0," the first switch 120 and the second switch 138 are turned on, entering an assist period where the brake is off.

As is apparent from the above, the present invention that uses such drive sources as the LR motor 74 and the UD motor 92 to achieve an electric brake permits configuring also an assist mechanism for assisting in bending the bending portion 24 that only requires addition of manipulating force detecting means such as the torque sensor 100 and use of the LR motor 74 and the UD motor 92 that constitute the brake without the need for adding drive sources such as motors.

In other words, the present invention using an electric mechanism to configure a brake for the bending portion 24 achieves reduction in the number of component parts as compared with mechanical brakes that use friction and reduction in weight and dimensions of the manipulating section 14 and still permits configuring not only a brake for the bending portion 24 but also an assist mechanism for assisting in bending. Thus, the present invention enables a significant reduction in load and fatigue on the part of the operator manipulating the endoscope 10 owing to a synergy produced by the effects of reduction in weight and dimensions of the manipulating section achieved by the provision of the brake and the effects of the bending assist.

Bending assist using the LR motor 74 and the UD motor 92 for constituting the brake for the bending portion 24 may be achieved in various manners other than by providing an assist with a force having a given ratio to a detected manipulating force as in the examples described above.

For instance, the manipulating force necessary for bending the bending portion 24 generally increases with the bend amount. The ratio of the force with which assist is provided through the LR motor 74 may be increased continuously or incrementally according to the increase in manipulating force applied to the LR knob 36.

Near the middle of the bending portion 24, where the bend amount is small, the control system tends to easily oscillate in response to the change in assist angle, and the necessary manipulating force is so small that no bending assist is required. Accordingly, when the manipulating force applied to the LR knob 36 is small, no assist through the LR motor 74 need be provided. In other words, a region that may be called "an insensitive zone" may be provided where the manipulating force is small to ensure that no assist is provided in such insensitive zone and that when a manipulating force beyond the insensitive zone is applied, assist may be provided according to the applied manipulating force.

Alternatively, in a region where the manipulating force is smaller than a given value, an assist force having a smaller ratio to the applied manipulating force may be provided than in the other regions. For instance, the insensitive zone may be replaced by a low-sensitivity range which is a region where the manipulating force is small and where the response (sensitivity) to the applied manipulating force is low, so that, in the low-sensitivity range, the ratio of the assisting force that is provided by the LR motor 74 to the manipulating force may be adjusted to be smaller than in the other regions (where the manipulating force exceeds the given value).

Conversely, when the manipulating force applied to the LR knob 36 is considerably great, the bending portion 24 may possibly have been caught in the human body or depressed with a great force onto the inside of the human body. In such a case, forcibly bending the bending portion 24 further may cause injuries to the human body such as an accidental perforation.

Accordingly, when the manipulating force applied to the LR knob 36 exceeds a given value, assist through the LR motor 74 may be discontinued.

Alternatively, when the manipulating force applied to the LR knob 36 exceeds a given value, the assist force produced by the motor 74 may be kept from increasing further and held constant. In other words, a limit may be set on the assisting force that is produced by the motor 74 depending on the manipulating force applied to the LR knob 36.

Further, when providing a bending assist through the LR motor 74 and the UD motor 92 according to the invention, the bending assist may be provided not only in any one of the above manners but also in a combination of two or more thereof.

For instance, a mode in which the insensitive zone is provided for a region where the manipulating force applied is small may be used in combination with a mode in which the assist through the LR motor 74 and the UD motor 92 is discontinued or a limit is set on the assist in a region where the manipulating force exceeds a given value.

Further, a mode in which the insensitive zone is provided and a mode in which the low-sensitivity region is provided may be combined to assign a first manipulating force to the insensitive zone and a second manipulating force greater than the first manipulating force to the low-sensitivity region, providing an assisting force having a higher ratio to the manipulating force when the manipulating force exceeds the second manipulating force.

Further, a mode in which the assisting force has a set limit and a mode in which the assisting force is discontinued may be combined so that a first manipulating force is provided with an assist having a force with a given ratio to the manipulating force, and a second manipulating force greater than the first manipulating force is provided with an assist having a constant force limited to the assisting force provided to the first manipulating force, no assist being provided when the manipulating force exceeds the second manipulating force.

While the endoscope of the invention has been described above in detail, the invention is by no means limited to the above embodiments, and various improvements and modifications may of course be made without departing from the spirit of the present invention.

We claim:

1. An endoscope having a bending portion close to a distal end of an insertion section, comprising:
    bending means for bending said bending portion;

manipulating means for performing bending operations of said bending portion;

drive means for bending said bending portion with said bending means;

bend amount detecting means for detecting a bend amount of said bending portion;

brake instructing means for giving a brake instruction to keep said bending portion in a bent state;

brake release means for giving a brake release instruction to discontinue maintenance of the bent state; and control means for controlling drive of said drive means, wherein, in response to the brake instruction given by said brake instructing means, said control means acquires the bend amount of said bending portion upon the brake instruction being given from said bend amount detecting means to drive said drive means so as to maintain the bend amount and, when the brake release instruction is given by said brake release means while the bent state is being maintained, gradually reduces a drive force of said drive means.

2. The endoscope according to claim 1, further comprising:

manipulating force detecting means for detecting a manipulating force applied to said manipulating means, wherein said control means assists said bending means in bending said bending portion through said drive means with a force applied with a given ratio to the manipulating force according to the manipulating force detected by said manipulating force detecting means.

3. The endoscope according to claim 2, wherein, when the brake instruction is given by said brake instructing means, said control means gradually reduces an assist drive force of said drive means corresponding to an assist in the bending to 0, and gradually increases a maintenance drive force of said drive means corresponding to the maintenance of the bend amount to maintain the bend amount.

4. The endoscope according to claim 2, wherein, upon the brake instruction being given by said brake instructing means, said control means reduces the assist drive force of said drive means corresponding to the assist in the bending to 0.

5. The endoscope according to claim 2, wherein said control means is provided with a first control mode for gradually reducing to "0" the assist drive force of said drive means corresponding to the assist in the bending in response to the brake instruction by said brake instructing means while gradually increasing the maintenance drive force of said drive means corresponding to the maintenance of the bend amount to maintain the bend amount, and a second control mode for reducing to 0 the assist drive force of said drive means corresponding to the assist in the bending upon the brake instruction being given by said brake instructing means, wherein said endoscope further comprises:

first selecting means for selecting one of the first control mode and the second control mode, and wherein said control means controls drive of said drive means according to a control mode selected by said first selecting means.

6. The endoscope according to claim 2, wherein when the brake release instruction is given, said control means gradually increases the assist drive force of said drive means corresponding to the assist in the bending to produce a force with a given ratio to the manipulating force.

7. The endoscope according to claim 2, wherein, upon the manipulating force being detected by said manipulating force detecting means after the brake release instruction is given, said control means reduces to 0 the maintenance drive force for said drive means corresponding to the maintenance of the bend amount.

8. The endoscope according to claim 2, wherein said control means is provided with a third control mode for gradually increasing the assist drive force of said drive means corresponding to the bending assist in response to the brake release instruction to produce a force with a given ratio to the manipulating force, and a fourth control mode for reducing to 0 the maintenance drive force of said drive means corresponding to the maintenance of the bend amount upon the manipulating force being detected by said manipulating force detecting means after the brake release instruction is given, wherein the endoscope further comprises:

second selecting means for selecting one of the third control mode and the fourth control mode, and wherein said control means controls drive of said drive means according to a control mode selected by said second selecting means.

9. The endoscope according to claim 1, wherein said bending means is provided to bend said bending portion by withdrawing a wire inserted into said bending portion, and wherein said bend amount detecting means detects the bend amount of said bending portion by detecting an angle of rotation of a pulley over which said wire is passed.

10. The endoscope according to claim 1, wherein said bending means is provided to bend said bending portion by withdrawing a wire inserted into said bending portion, and wherein said bend amount detecting means detects the bend amount of said bending portion by detecting a displacement of said wire.

11. The endoscope according to claim 1, wherein said bend amount detecting means detects the bend amount of said bending portion by detecting an angle of rotation of a gear engaged with said drive means.

12. The endoscope according to claim 1, wherein said bend amount detecting means detects the bend amount of said bending portion by detecting a bending angle of said bending portion.

* * * * *